United States Patent [19]

Peterson et al.

[11] 4,225,558

[45] Sep. 30, 1980

[54] FLUID SAMPLE TEST APPARATUS AND FLUID SAMPLE CELL FOR USE THEREIN

[75] Inventors: Dean M. Peterson, Littleton; Joseph R. Skovrinski, Denver, both of Colo.

[73] Assignee: Honeywell Inc., Minneapolis, Minn.

[21] Appl. No.: 943,705

[22] Filed: Sep. 19, 1978

[51] Int. Cl.² .................. G01N 1/10; G01N 21/24
[52] U.S. Cl. ................... 422/72; 356/246; 422/61; 233/26
[58] Field of Search ............ 422/61, 72; 233/26; 356/246

[56] References Cited

U.S. PATENT DOCUMENTS

| | | | |
|---|---|---|---|
| 3,532,470 | 10/1970 | Rochte | 422/61 |
| 3,689,224 | 9/1972 | Agnew et al. | 422/61 |
| 3,697,227 | 10/1972 | Goldstein et al. | 422/61 |
| 3,744,975 | 10/1973 | Mailen | 422/72 |
| 3,795,451 | 3/1974 | Mailen | 422/72 |
| 3,799,742 | 3/1974 | Coleman | 422/61 |
| 3,829,223 | 8/1974 | Hamel | 422/72 |
| 3,856,470 | 12/1974 | Cullis et al. | 422/72 |
| 3,873,217 | 3/1975 | Anderson et al. | 422/72 |

OTHER PUBLICATIONS

Laboratory Medicine, vol. 9, No. 6, Jun., 1978, pp. 8-20.

*Primary Examiner*—R. E. Serwin
*Attorney, Agent, or Firm*—Laurence J. Marhoefer; Lockwood D. Burton; Mitchell J. Halista

[57] ABSTRACT

A fluid test sample apparatus has a plurality of fluid test cells arranged on the periphery of a motor driven test cell tray. The fluids to be tested and respective reagents are introduced separately into corresponding test cells and are subsequently mixed in a reaction chamber for subsequent analysis by viewing the end product on the reaction through transparent walls of the reaction cell. The fluid samples and reagents are stored in separate radially displaced adjacent chambers and are mixed by a centrifugal force exerted thereon to force the fluids through the interconnecting internal passages in the tray into the reaction cell.

8 Claims, 3 Drawing Figures

FLUID SAMPLE TEST APPARATUS AND FLUID SAMPLE CELL FOR USE THEREIN

BACKGROUND OF THE INVENTION

Field of the Invention

The present invention is directed to fluid test apparatus. More specifically, the present invention is directed to a fluid test apparatus for providing an analysis of a plurality of fluid samples.

SUMMARY OF THE INVENTION

An object of the present invention is to provide an improved fluid test apparatus for multiple fluid samples.

In accomplishing this and other objects, there has been provided, in accordance with the present invention, a fluid test apparatus having a fluid storage tray with a plurality of fluid storage cells therein interconnected by internal passages in the tray. Fluids to be tested and reagents are initially stored in separate storage cells and introduced into a respective reaction chamber by rotation of the storage tray for subsequent analysis through transparent side walls of the reaction chamber. A fluid sump is located on the tray adjacent to each reaction chamber and is connected thereto by an internal passageway to store the overflow from the reaction chamber.

BRIEF DESCRIPTION OF THE DRAWINGS

A better understanding of the present invention may be had when the following detailed description is read in connection with the accompanying drawings, in which.

DESCRIPTION OF THE PREFERRED EMBODIMENT

Detailed Description

Figure 1:
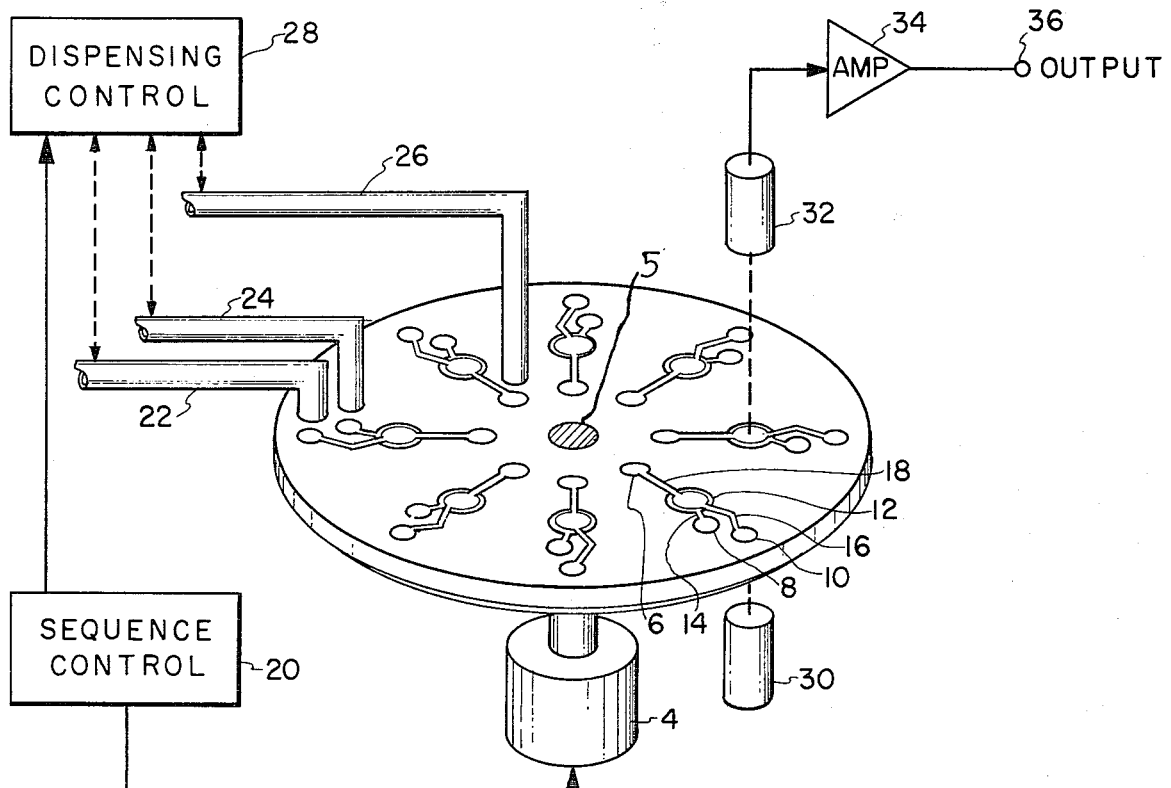
FIG. 1 is a pictorial illustration of an example of a fluid test apparatus embodying the present invention.

Referring to FIG. 1 in more detail, there is shown a fluid sample test apparatus for mixing a plurality of fluids to be tested with reagents and providing a visual inspection of the end products thereof. A fluid impervious storage tray 2 having a plurality of fluid storage locations therein has a center connection 5 to a motor 4 to be selectively rotated by the motor 4. Each of the fluid storage locations on the tray 2 includes a fluid sample well 6 a reagent well 8, an excess reagent sump 10 and a reaction cell, or chamber, 12. A first internal channel 14 is arranged to connect the reagent well 8 with the reaction cell 12 while a second channel 16 is arranged to connect the reaction cell 12 to the sump 10. A third channel 18 is arranged to connect the fluid sample well 6 to the reaction cell 12. The fluid sample well 6 is arranged on one side of the reaction cell 12 toward the center of the tray 2 while the reagent well 8 and sump 10 are arranged on the opposite side of the reaction cell 12 toward the periphery of the tray 2. The sample well 6, the reagent well 8 and the reaction chamber 12 may preferably be arranged on a common radial line of the tray 2.

The motor 4 is selectively driven by a sequence control 20 which is operated by either a predetermined automatic control or by an operator operating a manual keyboard or switches to advance the tray 2. At a first location adjacent to the surface of the tray 2 a source of a fluid sample (not shown) is connected to the sample well 6 by a flexible pipe 22 having an open end selectively positionable in a fluid-tight fluid passing relationship with the sample well 6. Concurrently, a source of a vacuum (not shown) is connected to the sump 10 by a second flexible pipe 24 having an open end which is positionable in fluid-tight contact with the sump 10. At a second location a third flexible pipe 26 is arranged to be selectively positionable to bring an open end thereof in fluid-tight contact with the fluid sample well 6. The third pipe 26 is used to supply a fluid sample from a fluid sample source (not shown) into the fluid sample well 6. The motion of the pipes 22, 24 and 26 into contact with the tray 2 are controlled by a dispensing control 28 which is operated synchronously with the motor 4 by the sequence control 20. The structure and operation of the dispensing control 28 and the pipes 22, 24 and 26 along with their associated fluid sample, reagent and vacuum sources are conventional and may be any suitable apparatus, such apparatus being well-known in the art. Accordingly, a further discussion of the structure and operation of these devices is believed to be unnecessary to provide a complete understanding of the present invention.

At a third location adjacent to the tray 2, a source of an inspection light 30 is arranged to direct an inspection beam through transparent side walls of the reaction cell 12 and into a light beam analysis detector 32. The output of the light beam detector 32 is amplified by an amplifier 34 and is applied to an output terminal 36. The operation of such detector analyzers is, also well-known in the art and a further discussion thereof is believed to be unnecessary. Additionally, it should be noted that while the pipes 22 and 24 have been shown at a first location and the pipe 26 at a second location, they could be located adjacent to each other and sequenced to provide reagent and sample filling at the same location, i.e., one position of the tray 2.

Figure 2:
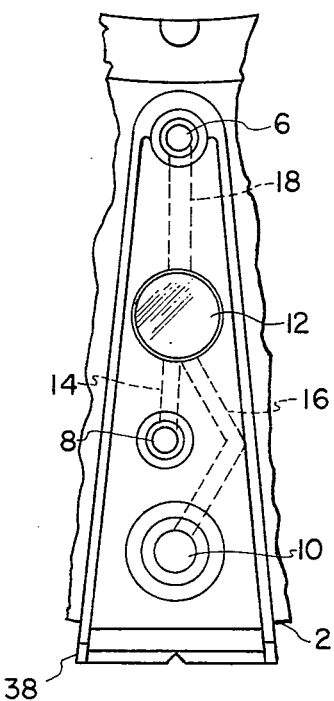
FIG. 2 is a magnified pictorial illustration of a portion of a fluid test apparatus as shown in FIG. 1
Figure 3:
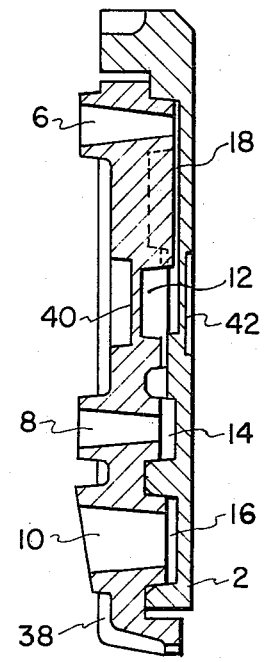
FIG. 3 is a magnified cross-section of a portion of the fluid test apparatus shown in FIGS. 1 and 2.

In FIGS. 2 and 3, there are shown magnified illustrations of the fluid storage and reaction cells for each of the fluid sample storage locations on the tray 2. As shown in the cross-section of FIG. 3, the tray 2 may be provided with a cover 38 at each of the fluid sample storage locations on the tray 2. The cover 38 is arranged to incorporate the fluid sample well 8, the reagent well 6 and the sump 10 as open-ended and tapered chambers extending therethrough. The cover 38 is also preferably molded from a transparent material and is arranged to form one side of the reaction cell 12 at a transparent area 40 of the cover 38. The tray 2 could be made of a similar transparent material and may have a thinner cross-section at an area 42 to improve the transparency thereof and to form the other side of the reaction cell 12. Alternatively either or both the cover 38 and the tray 2 may be made of a non-transparent material with transparent inserts forming the sides of the reaction cell 12. The cover 38 is spaced from the tray 2 and provided with appropriate passages to form the channels 14, 16 and 18. The cover 38 is adhesively fastened to the tray 2 to form a fluid-tight connection therebetween while providing the reaction cell 12 and the fluid-carrying channels 14, 16 and 18 interconnecting the fluid storage cells, as described above.

MODE OF OPERATION

In operation, tray 2 used in the example of the apparatus embodying the present invention shown in FIG. 1 is selectively positioned to enable each fluid sample storage location to be sequentially brought to the reagent filling, the fluid sample filling and the fluid analysis positions. Specifically, a location on the tray 2 is initially indexed by the sequence control 20 and the motor 4 to the fluid sample filling position wherein the pipe 22 is arranged to supply a fluid sample to the fluid sample well 8 while the pipe 24 concurrently applies a vacuum to the sump 10. The dispensing control 28 is then operated by the sequence control 20 to bring the open ends of the pipes 22 and 24 into fluid-tight contact with the well 6 and the sump 10, respectively. The fluid sample is dispensed from the fluid sample source (not shown) by any suitable means, e.g., a selectively operable valve, into the pipe 22 for transfer to the well 6. The fluid sample is, thus, initially introduced into the well 6 from the pipe 22. This fluid sample is subsequently drawn into the reaction cell 12 through the channel 14 under the urging of the vacuum applied to the sump 10 by the pipe 24. By presetting the time of the application of the sample and the vacuum, the reaction cell 12 is filled and any excess fluid sample is drawn into the sump 10 through the channel 16. Subsequently, the open ends of the pipes 22 and 24 are withdrawn from contact with the tray 2.

The tray 2 is then indexed to bring the next fluid storage location beneath the pipes 22 and 24 while the tray location with the previously stored fluid sample is positioned beneath the pipe 26. The dispensing control 28 is then operated to inject a second fluid sample into the well 6, as described above, and to bring the open end of the pipe 26 into fluid-tight contact with the well 8. The reagent in the pipe 26 is subsequently introduced into the well 8 with a predetermined quantity being metered therein by any suitable means (not shown). Following these injection operations, the sequence control 20 operates the dispensing control 28 to withdraw the pipes 22, 24 and 26 from the tray 2 and energizes the motor 4 to index the tray 2 to bring another fluid storage location beneath the open ends of the pipes 22 and 24 and the location just filled with a fluid sample beneath the open end of the reagent pipe 26. The subsequent operation is a repetition of that described above for a filling of a fluid sample and a reagent.

When the fluid storage locations to which a fluid sample and a reagent are to be added are filled (which may be less than all of the fluid storage locations), the sequence control 20 is actuated to energize the motor 4 to continuously spin the tray 2 at a predetermined rotary speed for a predetermined time. During this spin time, the reagent from the well 6 is forced by centrifugal force along the channel 18 into the reaction cell 12 where it mixes and reacts with the fluid sample therein. At the end of the aforesaid predetermined time, the spinning of the tray 2 is interrupted by the sequence control 20 to allow subsequent sequential interrogation of each reaction cell 12 by the light source 30. In other words, following the spin cycle of the tray 2, the tray 2 is sequentially advanced, or indexed, to bring each reaction cell having a reaction product therein in alignment with the light source 30 and analyzer 32. The resulting output signal from each analysis is applied in sequence to the output terminal 36 for appropriate use, e.g., recording.

The tray 2 and cover 38 are preferably made from an inexpensive material to permit the filled and analyzed tray to be a disposable item to avoid a cleaning operation thereof. Accordingly, the disposable tray 2 minimizes operator contact with the fluids involved, permits accurate control of fluid quantities and reaction time, provides a means for a plurality of concurrent reactions, minimizes the area requirements for plural reactions, permits custom adaptation to different fluid viscosities for adjacent tests and provides an integral reaction test cell for the reaction and evaluation thereof.

In order to facilitate the disposable nature of the present invention, the motor connection 5 may be any suitable quick disconnect positive drive with an index or cell tray locating means. For example, a simple form of the motor connection may include a turntable for supporting the tray with a keying pin projecting from the turntable for mating with a slot or depression in the cell tray. Such an arrangement would provide a positive drive to the tray with position keying while allowing the operator to quickly remove a used tray and insert a fresh tray for subsequent testing. The motor 4 would, or course, be connected to the turntable to rotate it and the cell tray as described above.

Accordingly, it may be seen that there has been provided, in accordance with the present invention, an improved multiple fluid test apparatus.

The embodiments of the invention in which an exclusive property or privilege is claimed are defined as follows:

1. A fluid test cell comprising
   a fluid impervious support tray,
   a plurality of fluid storage recesses located at each of a plurality of spaced peripheral locations on said tray,
   each of said fluid storage recesses at each location being either in a radially inward or a radially outward position with respect to a center of said tray and
   fluid conducting channels at each location connecting predetermined ones of said recesses,
   wherein said recesses at each location are at least three in number and are located on a common radial line of said tray and said channels at each location are located along said radial line, and including a fourth fluid sump recess at each location and a fluid conducting channel adjacent to said common radial line connecting said fourth recess to a center one of said three recesses on said radial line.

2. A fluid test cell as set forth in claim 1 wherein said tray includes a base and a cover at each location and wherein said channels are located between said cover and said base.

3. A fluid test cell as set forth in claim 2 wherein said cover includes fluid access ports to a radially outermost and radially innermost of said recesses along said common radial line of said tray and to said fourth recess at a corresponding location.

4. A fluid test cell as set forth in claim 3 wherein a center one of said recess at each location along said radial line has transparent sides to permit a visual inspection of the contents thereof.

5. A fluid test apparatus comprising a fluid impervious support tray,
   three fluid storage recesses within said support tray and located at each of a plurality of spaced peripheral locations on said tray along a common radial line of said tray, each of said fluid storage recesses at each location being either in a radially inward or a radially outward position with respect to a center of said tray fluid conducting channels at each location connecting predetermined ones of said recesses and being located along said radial line, one of said storage recesses at each location having transparent sides to permit a visual inspection of the contents thereof, a fourth fluid sump recess located at each of said spaced peripheral locations and a fluid conducting channel at each location adjacent to said radial line and connecting a center one of said three fluid recesses to said fourth fluid recess, drive means connected to said tray for selectively rotating said tray around a center thereof and analysis means located adjacent to said tray for selectively viewing the contents of said recesses having said transparent sides, wherein an innermost and outermost one of said recesses along said radial line and said fourth recess at each location includes a fluid supply port.

6. A fluid test apparatus as set forth in claim 5 and further including motor control means for selectively energizing said motor means to spin said tray in a first mode of operation and to successively index said locations past said analysis means in a second mode of operation.

7. A fluid test apparatus as set forth in claim 6 and further including fluid supply means located adjacent to said tray and controlled by said motor control means for selectively supplying a test fluid to said ports for said three recesses along said common radial line and a vacuum connection to said port for said fourth recess.

8. A fluid test apparatus as set forth in claim 7 wherein said analysis means including a light source arranged to project a light beam through said transparent sides and a light beam analyzer arranged to receive said light beam after passage through said transparent sides.

* * * * *